US006441146B1

(12) United States Patent
Minh

(10) Patent No.: US 6,441,146 B1
(45) Date of Patent: Aug. 27, 2002

(54) AFFINITY IMMOBILIZED METAL RESINS

(76) Inventor: Tran Quang Minh, Rue de l'Yser, 304, B-4430 Ans (BE)

( * ) Notice: Subject to any disclaimer, the term of this patent is extended or adjusted under 35 U.S.C. 154(b) by 0 days.

(21) Appl. No.: 09/352,620

(22) Filed: Jul. 13, 1999

Related U.S. Application Data
(60) Provisional application No. 60/092,654, filed on Jul. 13, 1998.

(51) Int. Cl.$^7$ ............................. B01J 20/26; C07K 1/16
(52) U.S. Cl. ..................... 530/417; 502/402; 525/50; 530/344; 556/116
(58) Field of Search ..................... 530/344, 412, 530/413, 415, 417; 210/656, 670, 674, 681, 682, 688, 690, 691, 692, 905; 525/50, 54.3, 180, 359.4, 379.38; 502/402; 436/86; 556/116, 134, 148

(56) References Cited

U.S. PATENT DOCUMENTS

| | | | |
|---|---|---|---|
| 3,821,126 A | * 6/1974 | Yamamoto et al. | ............ 521/32 |
| 4,423,158 A | 12/1983 | Porath | ............ 521/32 |
| 4,877,830 A | 10/1989 | Dobeli et al. | ............ 525/54.3 |
| 5,047,513 A | 9/1991 | Dobeli et al. | ............ 530/412 |

FOREIGN PATENT DOCUMENTS

| | | | |
|---|---|---|---|
| JP | 63-55117 | * | 3/1988 |
| JP | 63-56503 | * | 3/1988 |

OTHER PUBLICATIONS

Chemical Abstract 110: 39499j, Feb. 6, 1989.*
Brubaker et al, Flexidentate Chelation of . . . Inorganic Chemistry, vol. 5, No. 12, pp. 2110–2114, 1966.*
Translation of Japan Kokai 63–55117, Fractional Recovery Method of Gallium and Indium, Mar. 9, 1988.*
Translation of Japan Kokai 63–56503, Aminopolycarboxylic Acid–Type Chelote Resin And Its Manufacturing Method, Mar. 11, 1988.*
Nature vol. 258, Porath, et al., Metal Chelate Affinity Chromatography, A Anew Approach to Protein Fractionation, pp. 598–599, Dec. 18, 1975.
J. Coord. Chem., 1992 vol. 25. Coordination of Copper (II) to Polyaminopolycarbozylic Acids in Aqueous Solution, pp. 265–270, Micera, et al.
J. inorg. Nucl. Chem, 1971, vol. 33, pp. 809–816, Thermodynamics of the Interaction of Transition Metal Ions With Histamine, Rao, et al.
Acta Cryst. 1963 16, pp. 643–650, The Crystal Structure of Di (Histidino) Zincpentahydrate, Harding, et al.
J. Amer. Chem. Soc. 85, pp. 3736–3742, 1963, A Nuclear Magnetic Resonance Study of Structures of Cobalt (II)–Histidine Complexes, McDonald, et al.
88 (1969) Recueil, 411, Steroselectivity in the Complex Formationof Histodine With Cobalt (II) and Nickel (II), pp. 411–416, Ritsma, et al.
J. Coord. Chem., 1973, vol. 3, pp. 77–84, Histidine and Histamine Complexes of Copper and Zinc, Walker, et al.

(List continued on next page.)

Primary Examiner—Jeffrey E. Russel
(74) Attorney, Agent, or Firm—Knobbe, Martens, Olson & Bear, LLP

(57) ABSTRACT

Pentadentate chelators (PDC) resins are the metal chelate resins capable of forming the octahedral complexes with several polyvalent metal ions including $Cu^{2+}$, $Ni^{2+}$, $Zn^{2+}$ and $Co^{2+}$ with five coordination sites occupied by the chelator. This results in the best stability of the complexes and in one coordination site free for interaction and selective binding of accessible cysteine/histidine residues and chiefly histidine containing biomolecules such as proteins or peptides etc. Cu-PDC can be used as concentration resins to reduce the volume of a protein solution. It can be used also as a universal support for immobilizing covalently all proteins, using a soluble carbodiimide.

12 Claims, 2 Drawing Sheets

OTHER PUBLICATIONS

Inorganic Chemistry, vol. 12, No. 10, 1973, Structure of Sodium Nitrilotriacetatocopper (II), Monohydrate, Simon H. Whitlow, pp. 2286–2289.

Aust. J. Chem., 1970, 23, 1973, pp. 1973–1979, Imidazolato–Bridged Complexes of Copper (II), Bridson et al.

The Journal of Physical Chemistry, vol. 69, No. 2, Feb.1965, Infrared Spectra of Nitrilotriacetate Chelates in Aqueous Solution, Tomita, et al.

Journal of Chromatography, 411, (1987), 177–184, New Metal Chelate Adsorbent Selective For Proteins and Peptides Containing Neighbouring Histidine Residues, Dobeli, et al.

Biochemistry 1983, 22, pp. 1621–1630, American Chemical Society, Immobilized Metal Ion Affinity Adsorption and Immobilized Metal Ion Affinity Chromatography of Biomaterials. Serum Protein Affinities For Gel–Immobilized Iron and Nickel Ions.

* cited by examiner

AFFINITY IMMOBILIZED METAL RESINS

RELATED APPLICATION

This application claims priority under 35 U.S.C. §119(e) to U.S. Provisional Application No. 60/092,654, filed Jul. 13, 1998, incorporated herein by reference.

FIELD OF THE INVENTION

The present invention is related to new metal chelator resins and their manufacture process.

BACKGROUND OF THE INVENTION

Metal Chelate Affinity Chromatography (MCAC) (also denoted Immobilised Metal ion Affinity Chromatography (IMAC)) using affinity immobilised metal resins introduced by Porath et al. (Nature, 258, 589 (1975) and used for the purification of proteins which contain neighbouring histidine residues, has now become a powerful and versatile tool for the purification of natural and recombinant 6× His-tagged (or not) proteins and peptides.

The ligand used by these authors was the iminodiacetic acid (IDA). Electron paramagnetic resonance and absorption spectra studies have demonstrated that IDA is a tridentate ligand and the configuration of the complex IDA-$M^{2+}$ (1:1) with $M^{2+}$=bivalent metal ions, is a square or tetrahedral one (R. Dallocchio et al.; J. Coord. Chem., 25, 265 (1992). This explains why immobilised IDA can form a stable complex with the ion $Cu^{2+}$ and $Zn^{2+}$, but not with other heavy metal ions which need the octahedral configuration for a stable form.

It is also known that histidine is the only α-aminoacid capable of forming octahedral complexes with different polyvalent metal ions as follows: His—$M^{2+}$—His (B. Rao et al.; J. Inorg. Nucl. Chem.; 33, 809 (1971); M. M. Harding et al.; Acta Cryst., 16, 643 (1963)):

- Each histidine gives 3 coordination bonds to the $M^{2+}$ i.e. the 3-N group of the imidazole ring and the $NH_2$ and COOH groups of the aminoacid; the 1-NH group of the imidazole ring does not participate in the formation of the complexes (C. C. Mc Donald et al.; JACS, 85, 3736 (1963)).
- The complex formation is stereoselective (J. H. Rituma et al.; Recueil, 88, 411 (1969).
- The complex chemistry of histamine and imidazole has been described (W. R. Walker et al.; J. Coord. Chem., 3, 77 (1973); Aust. J. Chem., 23, 1973 (1970)).
- Furthermore, Single-crystal X-ray analysis (Simon H. Whitlow, Inorg. Chem., 12, 2286 (1973)) and Infrared Spectra studies (Y. Tomita et al.; JACS, 36, 1069 (1963) and J. Phys. Chem., 69, 404 (1965)) have demonstrated that Trisodium Nitrilotriacetate ($Na_3NTA$) is a tetradentate ligand for different polyvalent metal ions $M^{2+}$ and the corresponding complexes NTA-$M^{2+}$ have an octahedral configuration:
- At pH 5.5–10.0, NTA may be a mixture of $HN^+(CH_2—COO^-)_3$ and $N(CH_2—COO^-)_3$.
- Only the carboxylate and uncharged N groups participate in the coordination bonding. The carboxylic and charged N groups do not participate in such linkages.

The NTA derivatives immobilised on Agarose introduced by E. Hochuli et al. (J. Chromatogr., 411, 177 (1987)) and U.S. Pat. No. 4,877,830 (1989) can be therefore, an interesting method for the purification of histidine containing proteins. Their ligands are $H_2N—(CH_2)_n—CH(COOH)—N(CH_2—COOH)_2$ (n=2,4) and the resulting resins are: Resin-NH—$(CH_2)_n$—CH(COOH)—N $(CH_2—COOH)_2$ (n=2,4).

AIMS OF THE INVENTION

The present invention aims to provide new chelator resins having improved characteristics over the compounds of the state of the art and being suitable for metal chelate affinity chromatography.

The present invention is also related to the preparation process of such resins.

SUMMARY OF THE INVENTION

The present invention is related to an easy, rapid and inexpensive manufacture method of novel resins for IMAC and to said resins being hereafter called Pentadentate chelator (PDC) resins, which advantageously afford 5 coordination bonds to the $M^{2+}$ ions. Said coordination bonds may result in an improved stability of the obtained octahedral complexes and one coordination site is free for interaction and selective binding to accessible cysteine/histidine residues and chiefly histidine containing biomolecules that are preferably selected from the group consisting of proteins or peptides.

Furthermore, said PDC resins are able to chelate with different polyvalent metal ions including $Cu^{2+}$, $Ni^{2+}$, $Zn^{2+}$ and $Co^{2+}$ to give the corresponding metal chelate resins hereafter called Cu—PDC, Ni—PDC, Zn—PDC and Co—PDC respectively. These four resins will be thereafter used for the purification of histidine containing natural and recombinant proteins or peptides.

The present invention is also related to said PDC resins, for which the proteins cannot enter into the pores of the resin (molecular weights of proteins are greater than 5000 Daltons, by definition). Preferably, said resin is PDC-Sephadex® G-25 (obtained from Sephadex® G-25, Pharmacia, Uppsala, Sweden).

In addition, the binding of histidine containing proteins to the chelated metals depends on the complex Metal-PDC resins and the accessibility of histidine residues which in turn, depends on the configuration of the proteins of interest. Therefore, there is no universal rule that will predict the order of magnitude of binding of histidine containing biomolecules to $Cu^{2+}$, $Ni^{2+}$, $Zn^{2+}$ and $Co^{2+}$.

The present invention is also related to a PDC KIT consisting of four separate columns Cu—PDC, Ni—PDC, Zn—PDC and Co—PDC, that determine the most appropriate metal chelate resin suitable for the purification of natural and recombinant biomolecules, preferably selected from the group consisting of proteins or peptides.

The Cu-PDC resins according to the invention are used as universal supports for immobilising covalently proteins using a water-soluble carbodiimide and also as concentration resins to reduce the volume of a protein solution.

A last aspect of the present invention concerns the use of the pentadentate chelator (PDC) resins, and especially the PDC-Sephadex® G-25, according to the invention to obtain water and buffers free of polyvalent metal ions. In particular, the PDC-Sephadex® G-25 according to the invention is useful for preparing "metallo-proteins" free of heavy metal ions or proteins free of heavy metal ions after the Immobilised Metal ion Affinity Chromatography steps.

Figure 1:
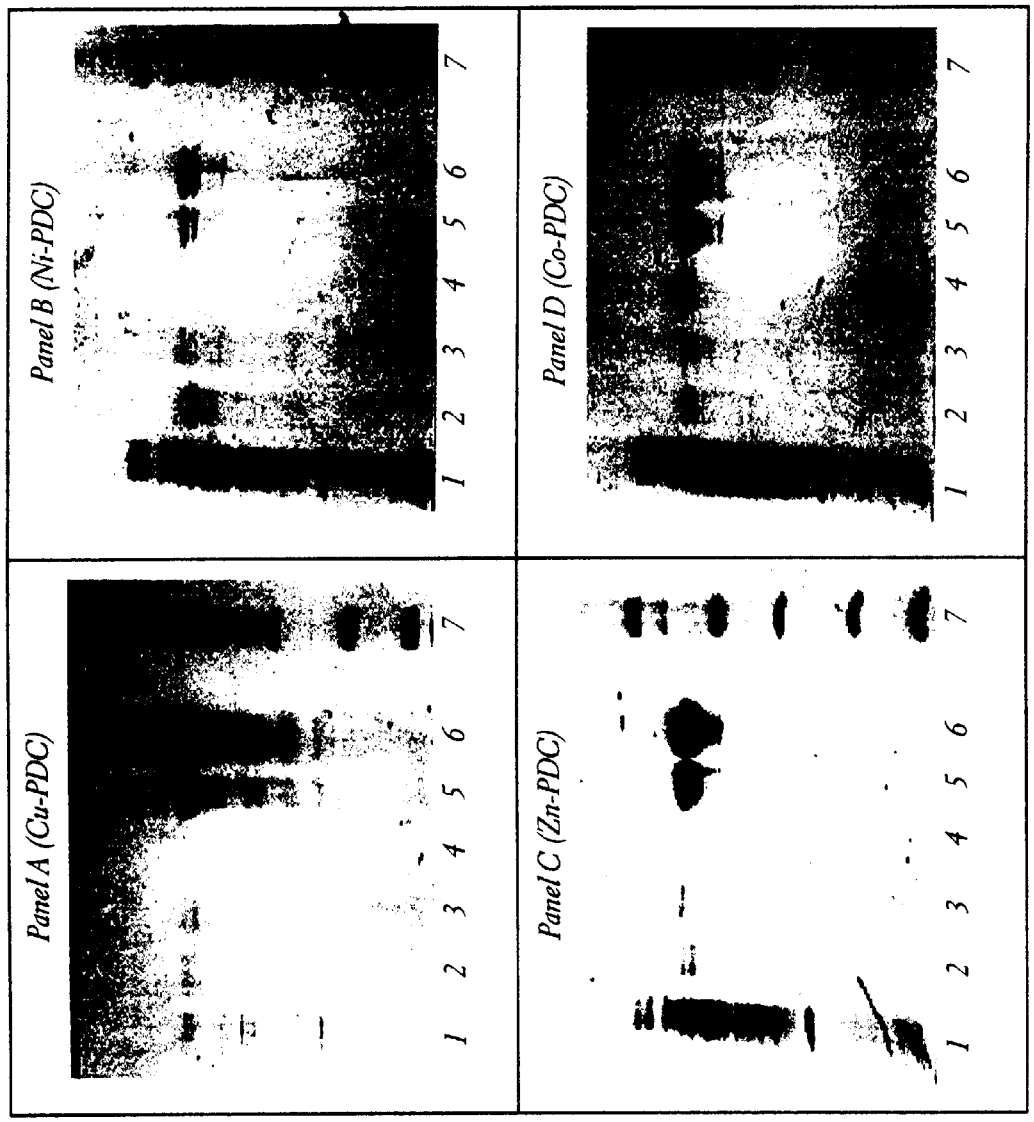
FIGS. 1A through 1D are a series of photographs of sodium dodecylsulfate-polyamide gel electrophoresis (SDS-PAGE) chromatography assays from purification experiments with heat shock protein from *Helicobacter pylori*
Figure 2:
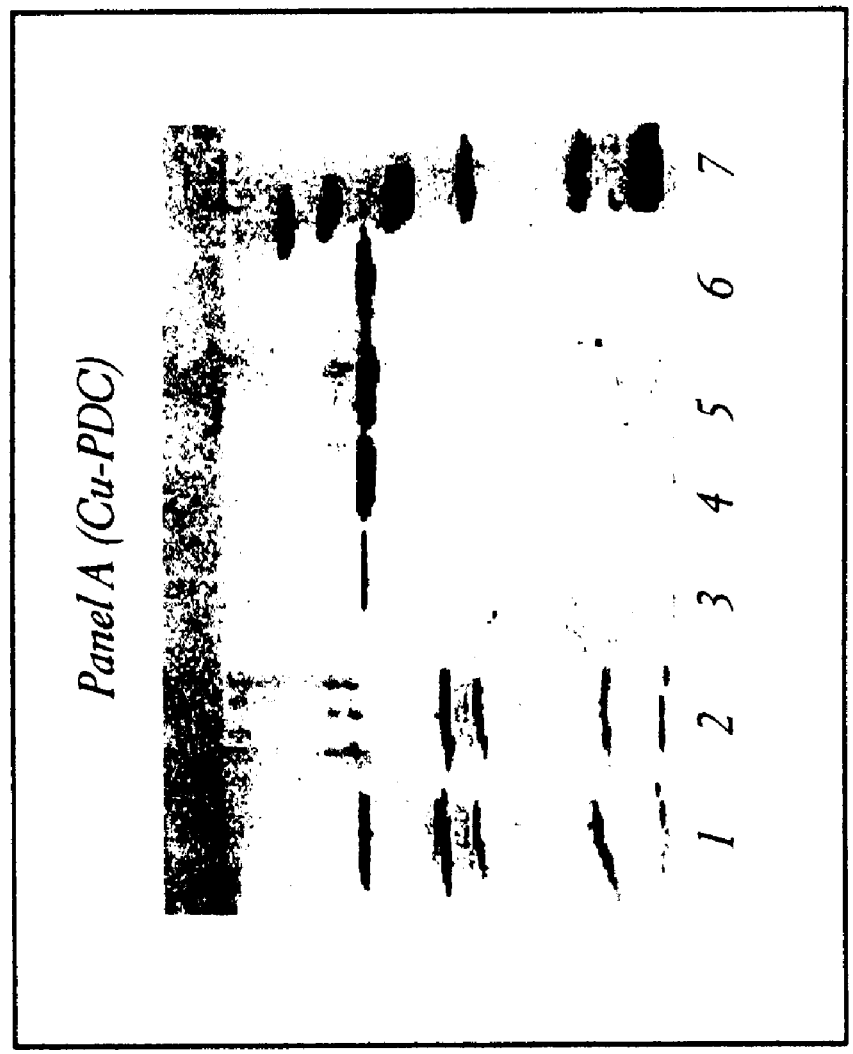

(HSP 60) expressed in E. coli, and stained with Coomassie blue. The pentadentate chelator kit in FIG. 1A was Cu—PDC, for FIG. 1B was Ni-PDC, for FIG. 1C was Zn—PDC and for FIG. 1D was Co—PDC. In each of the figures, the lanes were loaded as follows:

Lane 1: flow through and buffer A;
Lane 2: buffer A;
Lane3: buffer B;
Lane 4: buffer C;
Lanes 5 and 6: buffer E; and
Lane 7: Markers (97,400; 66,200; 45,000; 31,000; 21,000, and 14,400 daltons);
FIG. 2 is a photograph of SDS-PAGE assays from chromatography purification experiments with crude extract containing a mesophilic alkaline protease MW 50,000 Dalton (Zinc protein) from Pseudomonas aeruginosa IFO, stained with Coomasie blue using the Cu—PDC. The lanes were loaded as follows:
Lane 1: redissolved ammonium sulfate precipitate;
Lane 2: buffer A;
Lanes 3, 4, 5, 6: buffer B; and
Lane 7: Markers (97,400; 66,200; 45,000; 31,000; 21,500; and 14,400 daltons).

DETAILED DESCRIPTION OF THE INVENTION

As mentioned by Y. Tomita et al. (JACS, 36, p. 1069 (1963) and J. Phys. Chem. 690, 404 (1965)), at physiological pH, the NTA (nitrilotriacetate) and eventually immobilized NTA derivatives are the mixture of tridentate and tetradentate ligands for the metal ions $M^{2+}$. The concentration of octahedral complexes NTA-$M^{2+}$ may be therefore very smaller than the total NTA one, at physiological pH.

The pentadentate chelator (PDC) resins according to the invention, especially of the following formula, are the ideal solution of this problem: Resin-N($CH_2$—COOH)—($CH_2$)$_4$—CH(COOH)—N($CH_2$—COOH)$_2$. At physiological pH, said resins are a mixture of tetradentate and pentadentate ligands for the metal ions $M^{2+}$. The concentration of octahedral complexes PDC—$M^{2+}$ is therefore optimal as well as their corresponding capacity for histidine containing proteins.

The present invention is also related to the manufacture process of a compound of formula. Resin-ω-N-Lysine synthesised by reaction between Bia-Lysine-$M^{2+}$, especially the Bis-Lysine-$Cu^{2+}$ and an activated resin of formula: Resin-O—$CH_2$-ethylenepoxide or any other activated matrix being able to react with —$NH_2$ containing organic compounds. Preferably, the carrier matrix used in the above process can be any functionalised or activated resins used for the manufacture of affinity resins, preferably a resin selected from the group consisting of Sepharose® CL-4B, CL-6B, Fast Flow, and Sephadex® G-25 resins (Pharmacia, Uppsala, Sweden), Cellulose and/or Cotton.

The present invention concerns also a reaction process of said Resin-ω-N-Lysine with an excess of halogenoacetic acid, preferably bromoacetic acid, in a basic medium, which allows the formation of the pentadentate resin according to the invention: Resin-ω-N-Lysine+Br—$CH_2$COOH in basic media → Resin-N($CH_2$—COOH)—($CH_2$)$_4$—CH(COOH)—N($CH_2$—COOH)$_2$.

The present invention will be described in details in reference to the enclosed non-limiting examples.

EXAMPLES

Example 1

75 g of Lysine monochlorhydrate were dissolved in a solution of 33 g of sodium hydroxide and 330 ml of distilled water. To this solution, was added a solution of 51.6 g of $CuSO_4$ in 150 ml of distilled water (heated at 30° C. until complete dissolution). The corresponding complex was used for the following operations without purification. (However, purification could be carried out by adding ethanol until the formation of a non-miscible phase).

Example 2

300 ml of Sepharose® CL-4B abundantly washed with distilled water, were activated with 195 ml of NaOH 2M diluted in 450 ml of distilled water and 75 ml of epichlorhydrin at 40° C. for 2 hours. The corresponding activated resin was washed with distilled water until neutral pH was achieved. To this activated resin, were added 150 ml of NaOH 2M and the solution prepared in Example 1. The mixture was stirred mildly at 40° C. for 3 hours and then at 50° C. overnight.

The resulting resin was washed abundantly with the distilled water until the pH of the waste water reached 7.0, then abundantly with an aqueous diluted acid solution and finally with an excess of distilled water, until the complete decoloration of the resin. This resin was sufficiently pure for the following operations.

Example 3

To 300 ml of the resin prepared in Example 2, were added 405 ml of NaOH 2M and a solution of 75 g of bromoacetic acid and 270 ml of NaOH 2M. The mixture was stirred at 4° C. for 3 hours and then overnight at room temperature. The resin was washed abundantly with distilled water until the pH of the wastewater reached 7.0 and was stored in NaCl 0.5M, in the presence of $NaN_3$ 0.02% (w/v).

Example 4

To a solution of 10.g of $MCl_2$ or $MSO_4$ (M=Cu or Zn or Ni or Co) in 800 ml of distilled water, were added 300 ml of the resin prepared in Example 3. The mixture was stirred gently for 5 minutes. The metal chelated resin was filtered off, washed 3 times with 500 ml of distilled water, 3 times with Too ml of $NaH_2PO_4$ 0.1M pH 4.0, 3 times with 500 ml of $NaH_2PO_4$ 0.1M pH 8.0 and finally once with 500 ml of $NaH_2PO_4$ 0.1M pH 7.5. The resin was stored in $NaH_2PO_4$ 0.1M pH 7.5 in the presence of $NaN_3$ 0.05% (w/v). The such obtained resins were named respectively Cu—PDC, Ni—PDC, Zn—PDC and Co—PDC.

Example 5

Four resins, i.e. Cu—PDC, Ni—PDC, Zn—PDC and Co—PDC obtained in Example 4, were loaded separately into four small polyethylene columns to reach 1 ml of resin in each. The set of these four columns was named the PDC KIT. In the following examples 6, 7, 8, 9, 10, the purification of the proteins of interest using the PDC KIT was obtained as follows.

Each column was equilibrated with 2 ml of the phosphate buffered saline (PBS) $NaH_2PO_4$ 50 mM, NaCl 300 mM pH 7.5; $NaN_3$ 0.1% (w/v) (buffer A).

The crude clarified lysate containing the protein of interest in buffer A, was loaded onto each column as indicated in each case.

Each column was then washed three times with 2 ml of buffer A, three times with 2 ml of buffer B (buffer A+urea 4M pH 7.5), three times with 2 ml of buffer C (buffer A+urea 8M pH 7.5), once with 2 ml of buffer D (buffer A adjusted to pH 6.0) and finally once with 2 ml of buffer A.

Each column was eluted three times with 2 ml of buffer E (buffer A+imidazole 100 mM pH 7.5) and three times with 2 ml of buffer F (buffer A+imidazole 200 mM pH 7.5).

The fractions obtained from each step of the purification were assayed using the most appropriate system e.g. O.D. at 280 nm, Sodium dodecylsulfate-polyacrylamide gel electrophoresis (SDS-PAGE), etc.

Example 6

Purification of Proteins by Using the PDC Kit (as Described in Example 5)

The crude clarified lysate of 6× His-tagged HSP 60 (heat shock protein) from *Helicobacter pylori* expressed in *E. coli* (concentration of HSP60: approx. 5 mg/ml)

Sample volume that was loaded onto each column of PDC KIT; 500 microliter.

FIGS. 1A through 1D show the results of the SDS-PAGE assays for Cu—PDC, Ni—PDC, ZN—PDC and Co—PDC, respectively. Zn—PDC allowed the purification of HSP 60 in a single step with a recovery of 15 mg of protein per ml of wet gel (Panel C, lanes 5 and 6).

Example 7

Purification of Protein by Using the PDC Kit (as Described in Example 5)

The crude clarified lysate of 6× His-tagged Urease from *Helicobacter pylori* expressed in *E. coli* (concentration of urease: approx. 1 mg/ml)

Sample volume that was loaded onto each column of the PDC KIT: 2 ml.

Results:

Ni—PDC can be used to purify the native urease and Zn—PDC to obtain the α-chain (MW 60,000 Dalton) and the β-chain (MW 30,000 Dalton) of urease, clearly demonstrated by SDS-PAGE.

Example 8

Purification of Protein by Using the PDC Kit (as Described in Example 5)

The crude clarified lysate of 6× His-tagged Penicillin binding protein 5 (MW 70,000 Dalton) from *E. coli* (concentration of Penicillin binding protein 5: approx. 0.1 mg/ml)

Sample volume that was loaded onto each column of the PDC KIT: 2 ml.

Results:

Ni—PDC is the best for this purification, clearly demonstrated by SDS-PAGE.

Example 9

Purification of Protein by Using the PDC Kit (as Described In Example 5)

The crude extract (redissolved ammonium sulfate precipitate) containing a mesophilic alkaline protease MW 50,000 Dalton (Zinc protein) from *Pseudomonas aeruginosa* IFO (Institute of fermentation of Osaka 3455 (concentration of alkaline protease: approx. 1 mg/ml)

Sample volume that was loaded onto each column of the PDC KIT: 1 ml.

No binding of the protein to Ni, Zn, and Co—PDC columns was observed. FIG. 2 shows the results of SDS-PAGE assays from Cu—PDC. Cu—PDC was the only chelate gel allowing the purification of this protease in a single step (See lanes 4, 5, 6).

Example 10

Purification of Protein by Using the PDC Kit (as Described in Example 5)

Sample volume that was loaded onto the column: 10 ml of crude clarified lysate of mutated triosephosphate isomerase from *E. coli*, containing 8 histidine residues (5 accessible).

Results:

Ni—PDC allowed the purification of mutated triosephosphate isomerase in a single step with a recovery of 15 mg of protein/ml of wet gel, clearly demonstrated by SDS-PAGE.

Example 11

A solution of 10 mg of human Thyroxine binding globulin (TBG) dissolved in 50 ml of buffer A (see Example 5), was loaded onto the 1 ml Cu—PDC column. The optical density at 280 nm of the flow-through indicated that the totality of TBG was retained by the column. The recovery of TBG eluted by 2 ml of buffer E (see Example 5) was approximately 95% (9.5 mg). Its activity determined by RIA (radioimmunoassay), was revealed unaffected.

Example 12

20 mg of bovine serum albumin (BSA) dissolved in 5 ml of buffer A (see Example 5), were mixed during 15 minutes with 1 ml of Cu—PDC resin pre-equilibrated with the same buffer. The suspension was filtered off, washed respectively with 5 ml of buffer A adjusted to pH 8.0, 5 ml of buffer A adjusted to pH 4.0 and with 5 ml of buffer A adjusted to pH 5.5.

The optical density at 280 nm of the filtrates of each washing step indicated that the quasi-totality of BSA was retained by the Cu—PDC resin.

A solution of 10 mg of 1-ethyl 3-(3-dimethylaminopropyl)carbodiimide hydrochloride dissolved in 1 ml of distilled water, was added to the suspension of 1 ml of complex BSA-Cu—PDC resin obtained previously, in 4 ml of buffer A pH 5.5. The mixture was shaken mildly overnight at 4° C.

The resin was filtered off, washed abundantly with the buffer A. The $Cu^{2+}$ ions were stripped from the resin with EDTA (ethylenediaminotetraacetic acid) 0.1M pH 7.4. The resin was then washed with 25 ml of buffer A adjusted to pH 4.0, 25 ml of buffer A adjusted to pH 8.0 and stored in buffer A pH 7.5.

The recovery of a such covalent immobilisation i.e. BSA-PDC, was quantitative.

Example 13

100 ml of 1 g of bovine serum albumin (BSA) in buffer A (see Example 5) containing 5 mg of $CuCl_2$, 5 mg of $Ni_2SO_4$, 5 mg of $ZnCl_2$, 5 mg of $COCl_2$ and 1 mg of $CaCl_2$ was loaded onto a large section column containing 10 ml of PDC-Sephadex® G-25. The solution of BSA such obtained was free of polyvalent metal ions.

What is claimed is:

1. A pentadentate chelator resin having the formula:

Resin-N $(CH_2-COOH)-(CH_2)_4-CH(COOH)-N(CH_2-COOH)_2$, wherein said resin has pores which do not allow penetration by proteins having a molecular weight higher than 5000 Daltons.

2. A method for the generation of water and/or buffers free of heavy metal ions, comprising contacting the water and/or buffers containing heavy metal ions with the pentadentate chelator resin according to claim 1.

3. A method for the preparation of proteins obtained after an Immobilised Metal Ion affinity Chromatography, free of heavy metal ions comprising contacting a solution comprising said proteins with the pentadentate chelator resin according to claim 1.

4. A method for the preparation of metalloproteins free of heavy metal ions, comprising performing a gel filtration of the metalloproteins on the pentadentate chelator resin of claim 1 and stripping the heavy metal ions from the pentadentate chelator resin.

5. A pentadentate chelator kit (PDC-kit) comprising four separated pentadentate chelator resins, wherein each of said resins is coordinated to a different divalent metal ion, wherein the divalent metal ions are $Cu^{2+}$, $Zn^{2+}$, $Ni^{2+}$, and $Co^{2+}$.

6. A method for the purification of natural and/or recombinant proteins or peptides, comprising contacting the proteins or peptides with the pentadentate chelator kit according to claim 5.

7. The method according to claim 6, wherein the natural and/or recombinant proteins contain one or more histidine residues.

8. A method for the preparation of a column for covalently immobilizing a protein, said column comprising a pentadentate chelator (PDC) resin having the formula Resin-N($CH_2$—COOH)—($CH_2$)$_4$—CH(COOH)—N($CH_2$—COOH)$_2$, comprising:

reacting an appropriately activated carrier matrix of a porous resin with a metal chelator having the formula: Bis-Lysine-$Cu^{2+}$, in order to form a compound having the formula: Resin-ω-N-Lysine;

reacting said compound having the formula: Resin-ω-N-Lysine, to form the pentadentate chelator resin; and contacting said resin with a composition comprising said protein.

9. The method according to claim 8, further comprising recovering the pentadentate chelator resin.

10. A method for covalent immobilization of a protein comprising:

contacting the protein with the pentadentate chelator resin having the formula Resin-N ($CH_2$—COOH) —($CH_2$)$_4$—CH(COOH)—N($CH_2$—COOH)$_2$, wherein the pentadentate chelator resin is coordinated with divalent metal $Cu^{2+}$, said contacting thereby forming a protein-PDC $Cu^{2+}$ resin complex;

contacting the protein-PDC $Cu^{2+}$ resin complex with a water soluble carbodiimide; and removing the divalent metal $Cu^{2+}$ from the protein-PDC $Cu^{2+}$ resin complex.

11. The method according to claim 10, wherein the divalent metal $Cu^{2+}$ is removed from the protein-PDC $Cu^{2+}$ resin complex with ethylenediaminotetraacetic acid (EDTA) in order to obtain the protein covalently attached to the PDC resin.

12. A method for reducing the volume of a protein solution, comprising:

contacting the protein with the pentadentate chelator resin having the formula Resin-N ($CH_2$—COOH) —($CH_2$)$_4$—CH(COOH)—N($CH_2$—COOH)$_2$, wherein the pentadentate chelator resin is porous and coordinated with divalent metal $Cu^{2+}$, said contacting thereby forming a protein-PDC $Cu^{2+}$ resin complex; and eluting the protein from the PDC $Cu^{2+}$ resin.

* * * * *